United States Patent
Tkaczyk et al.

(10) Patent No.: US 7,450,683 B2
(45) Date of Patent: Nov. 11, 2008

(54) TILEABLE MULTI-LAYER DETECTOR

(75) Inventors: John Eric Tkaczyk, Delanson, NY (US); Jonathan David Short, Saratoga Springs, NY (US); James Walter Leblanc, Niskayuna, NY (US); James Wilson Rose, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 237 days.

(21) Appl. No.: 11/516,852

(22) Filed: Sep. 7, 2006

(65) Prior Publication Data
US 2008/0061395 A1    Mar. 13, 2008

(51) Int. Cl.
*A61B 6/00* (2006.01)
(52) U.S. Cl. .................. 378/19; 378/98.8; 250/370.08
(58) Field of Classification Search .................. 378/19, 378/98.8; 250/208.1, 370.08, 370.09, 370.11
See application file for complete search history.

(56) References Cited

U.S. PATENT DOCUMENTS

| 6,553,092 B1 | 4/2003 | Mattson et al. ............... 378/19 |
| 2005/0006588 A1 | 1/2005 | Fuchs et al. .................. 250/367 |
| 2005/0253079 A1 | 11/2005 | Hoffman ............... 250/370.13 |
| 2005/0259783 A1 | 11/2005 | Hoffman ..................... 378/19 |

*Primary Examiner*—Courtney Thomas
(74) *Attorney, Agent, or Firm*—Jason K. Klindtworth

(57) ABSTRACT

A detector assembly is presented. The detector assembly includes a first detector layer having a top side and a bottom side, where the first detector layer includes a plurality of first coupling gaps. Additionally, the detector assembly includes a first interconnect structure operationally coupled to the first detector layer and configured to facilitate transfer of a first set of image data from the first detector layer to backplane electronics. The detector assembly also includes a second detector layer having a top side and a bottom side and disposed adjacent the bottom side of the first detector layer, where the second detector layer includes a plurality of second coupling gaps configured to facilitate passage of the first interconnect structure from the first detector layer to the backplane electronics. Also, the detector assembly includes a second interconnect structure operationally coupled to the second detector layer and configured to facilitate transfer of a second set of image data from the second detector layer to the backplane electronics.

36 Claims, 9 Drawing Sheets

TILEABLE MULTI-LAYER DETECTOR

BACKGROUND

The invention relates generally to radiographic detectors for diagnostic imaging, and more particularly to large area detectors for high flux rate imaging, such as in computed tomography (CT) applications.

Radiographic imaging systems, such as X-ray and computed tomography (CT) have been employed for observing, in real time, interior aspects of an object. Typically, the imaging systems include an X-ray source that is configured to emit X-rays toward an object of interest, such as a patient or a piece of luggage. A detecting device, such as an array of radiation detectors, is positioned on the other side of the object and is configured to detect the X-rays transmitted through the object.

Conventional CT and other radiographic imaging systems utilize detectors that convert radiographic energy into current signals that are integrated over a time period, then measured and ultimately digitized. A drawback of such detectors however is their inability to count at the X-ray photon flux rates typically encountered with conventional CT systems. Additionally, conventional detectors also lack the ability to track the energy of incident x-rays. For example, photon counting direct conversion detectors are known to suffer from decreased detection quantum efficiency (DQE) at high count rates mainly due to detector pile-up. Further, very high X-ray photon flux rate has been known to cause pile-up and polarization that ultimately leads to detector saturation. In other words, these detectors typically saturate at relatively low X-ray flux level thresholds. Above these thresholds, the detector response is not predictable or has degraded dose utilization. That is, once a pixel is saturated (corresponding to a bright spot in the generated signal), additional radiation will not produce useful detail in the image.

Previously conceived solutions to enable photon counting at high X-ray flux rates include employing pixels having a relatively small size to achieve higher spatial resolution and reduce flux rate sensitivity. Unfortunately, this reduction in the pixel size results in increased cost.

Additionally, applications such as medical and industrial imaging, NDE, security, baggage scanning, astrophysics and medicine may entail the use of larger coverage detectors that encompass large areas. In the field of medical diagnostics, such as, but not limited to, computed tomography (CT), ultrasound and mammography, it may be desirable to employ larger detectors to facilitate acquisition of image data from a large portion of the anatomy in a single gantry rotation thereby enhancing image quality.

Previously conceived solutions to obtaining wider coverage involved increasing the number of rows of detector elements. Arrays of detectors have also been utilized to circumvent the problems associated with employing single large area detectors. The X-Y plane may be employed for assembling the detectors arrays to facilitate the construction of large area detectors arrays. However, such arrays can be very dense and necessitate a large quantity of control and amplifier electronics to drive the individual detectors of the array. Presently, the control and amplifier electronics employed to drive the individual detectors are also positioned in the X-Y plane resulting in a large footprint and potentially, gaps in the detector area due to the need to locate electronics in or adjacent to the detector. Furthermore, the density of input/output (I/O) required for coupling the individual detectors with the associated electronics may be very high. Also, the density of I/O may be too large for traditional interconnect strategies to handle. Presently, the interconnect lengths required to couple the detector elements to the electronic device are very long. It would be desirable to minimize interconnect lengths in order to circumvent problems associated with longer interconnect lengths, such as, effects of capacitance, and degraded signal quality.

There is therefore a need for a design of a detector that does not saturate at the X-ray photon flux rates typically found in conventional radiographic systems. In particular, there is a significant need for a design that advantageously enhances the flux rate in detectors that will allow photon counting with energy discrimination in medical and industrial applications that are heretofore unmanageable because either the flux rate or the dynamic range requirements are too high. Additionally, there is a particular need to assemble large area detector arrays in order to circumvent associated problems, such as, complexities and costs associated with manufacturing. Furthermore, it would be desirable to position the associated electronics in close proximity to the individual detector elements of the detector array in order to minimize system size, complexity, interconnect lengths and enhance the performance of the detector arrays.

BRIEF DESCRIPTION

Briefly, in accordance with aspects of the technique, a detector assembly is presented. The detector assembly includes a first detector layer having a top side and a bottom side, where the first detector layer includes a plurality of first coupling gaps. Additionally, the detector assembly includes a first interconnect structure operationally coupled to the first detector layer and configured to facilitate transfer of a first set of image data from the first detector layer to backplane electronics. The detector assembly also includes a second detector layer having a top side and a bottom side and disposed adjacent the bottom side of the first detector layer, where the second detector layer includes a plurality of second coupling gaps configured to facilitate passage of the first interconnect structure from the first detector layer to the backplane electronics. Also, the detector assembly includes a second interconnect structure operationally coupled to the second detector layer and configured to facilitate transfer of a second set of image data from the second detector layer to the backplane electronics.

In accordance with further aspects of the technique, a detector assembly is presented. The detector assembly includes a first detector module, where the first detector module includes a first detector layer having a top side and a bottom side, where the first detector layer includes a plurality of first coupling gaps, a first interconnect structure operationally coupled to the first detector layer and configured to facilitate transfer of a first set of image data from the first detector layer to backplane electronics, and a first set of electronics disposed adjacent the first interconnect structure, where the first set of electronics is in operative association with the first interconnect structure and configured to process the first set of image data. In addition, the detector assembly includes at least a second detector module, where the second detector module includes a second detector layer having a top side and a bottom side, where the second detector layer includes a plurality of second coupling gaps configured to facilitate passage of the first interconnect structure from the first detector layer to the backplane electronics, a second interconnect structure operationally coupled to the second detector layer and configured to facilitate transfer of a second set of image data from the second detector layer to the backplane electronics, and a second set of electronics disposed adjacent the second interconnect structure, where the second set of electronics is in operative association with the second interconnect structure and configured to process the second set of image data.

In accordance with yet another aspect of the technique, a method of imaging is presented. The method includes obtaining a first set of image data from a first detector layer in a detector assembly having a first detector layer and a second detector layer, where the first detector layer includes a plurality of first coupling gaps. Further, the method includes obtaining a second set of image data from a second detector layer, where the second detector layer comprises a plurality of second coupling gaps configured to facilitate passage of a first interconnect structure from the first detector layer to backplane electronics. The method also includes interpolating the second set of image data.

In accordance with further aspects of the technique, an imaging system is presented. The imaging system includes a source of radiation configured to emit a stream of radiation toward a patient to be scanned and a computer configured to generate images with enhanced image quality and to provide tissue composition information. Further, the imaging system also includes a detector assembly configured to detect the stream of radiation and to generate one or more signals responsive to the stream of radiation, where the detector assembly includes a first detector layer having a top side and a bottom side where the first detector layer comprises a plurality of first coupling gaps, a first interconnect structure operationally coupled to the first detector layer and configured to facilitate transfer of a first set of data from the first detector layer to backplane electronics, a second detector layer having a top side and a bottom side and disposed adjacent the bottom side of the first detector layer, where the second detector layer comprises a plurality of second coupling gaps configured to facilitate passage of the first interconnect structure from the first detector layer to the backplane electronics, and a second interconnect structure operationally coupled to the second detector layer and configured to facilitate transfer of a second set of data from the second detector layer to the backplane electronics. Additionally, the imaging system includes a system controller configured to control the rotation of the source of radiation and the detector assembly and to control the acquisition of one or more sets of projection data from the detector assembly via a data acquisition system, and a computer system operationally coupled to the source of radiation and the detector assembly, where the computer system is configured to receive the one or more sets of projection data.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Figure 1:
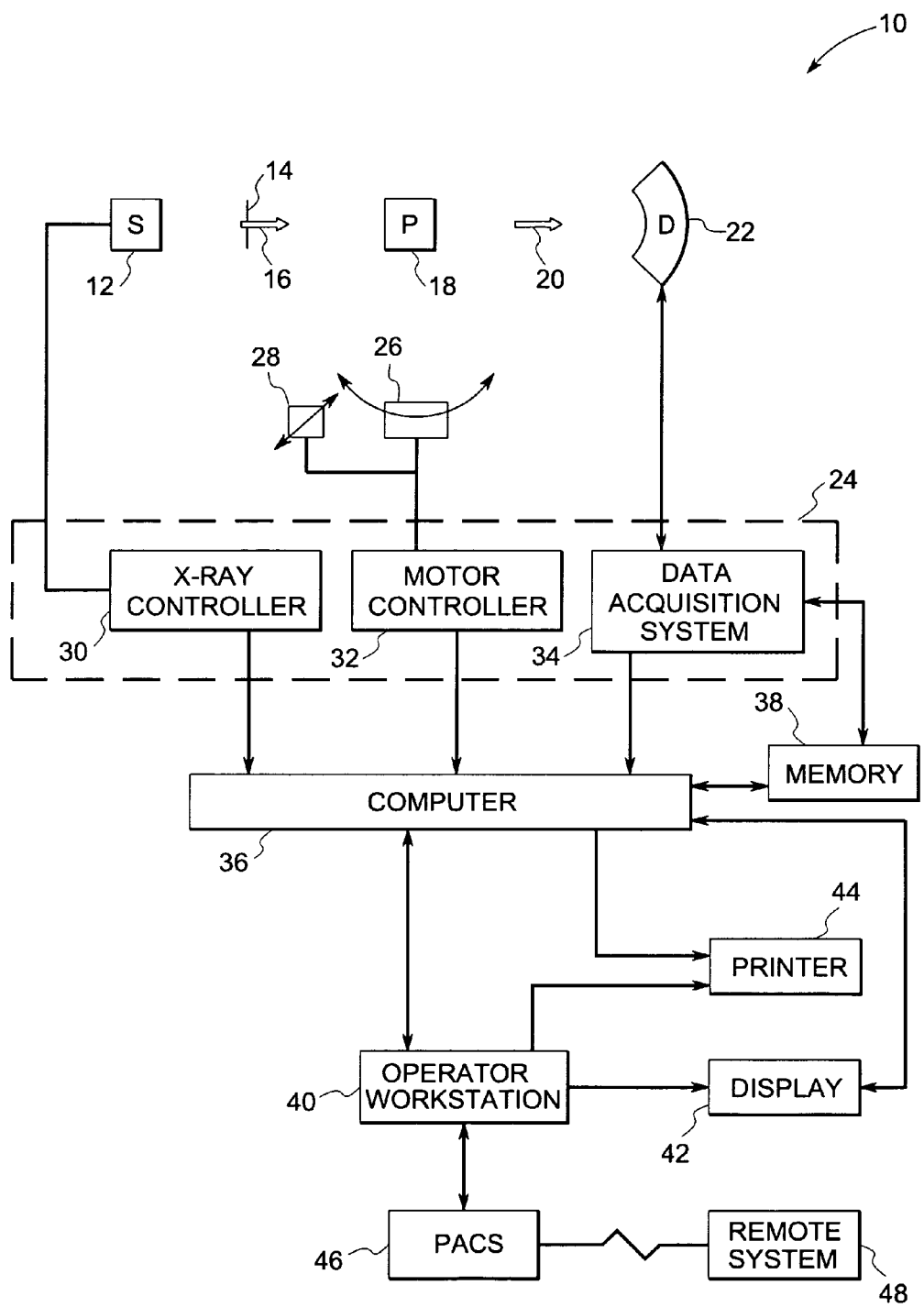
FIG. 1 is a block diagram of an exemplary imaging system in the form of a CT imaging system for use in producing processed images.

FIG. 1 is a block diagram showing an imaging system 10 for acquiring and processing image data in accordance with the present technique. In the illustrated embodiment, the system 10 is a computed tomography (CT) system designed to acquire X-ray projection data, to reconstruct the projection data into an image, and to process the image data for display and analysis in accordance with the present technique. In the embodiment illustrated in FIG. 1, the imaging system 10 includes a source of X-ray radiation 12. In one exemplary embodiment, the source of X-ray radiation 12 is an X-ray tube. The source of X-ray radiation 12 may include one or more thermionic or solid-state electron emitters directed at an anode to generate X-rays or, indeed, any other device capable of generating X-rays having a spectrum and energy useful for imaging a desired object. Examples of suitable electron emitters include tungsten filament, tungsten plate, field emitter, thermal field emitter, dispenser cathode, thermionic cathode, photo-emitter, and ferroelectric cathode.

The source of radiation 12 may be positioned near a collimator 14, which may be configured to shape a stream of radiation 16 that is emitted by the source of radiation 12. The stream of radiation 16 passes into the imaging volume containing the subject to be imaged, such as a human patient 18. The stream of radiation 16 may be generally fan-shaped or cone-shaped, depending on the configuration of the detector array, discussed below, as well as the desired method of data acquisition. A portion 20 of radiation passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

The radiation source 12 is controlled by a system controller 24, which furnishes both power, and control signals for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, the system controller 24 is coupled via a motor controller 32 to a rotational subsystem 26 and a linear positioning subsystem 28. In one embodiment, the rotational subsystem 26 enables the X-ray source 12, the collimator 14 and the detector 22 to be rotated one or multiple turns around the patient 18. In other embodiments, the rotational subsystem 26 may rotate only one of the source 12 or the detector 22 while the system controller 24 may differentially activate various stationary electron emitters to generate X-ray radiation if the detector 22 is rotated and/or detector elements arranged in a ring about the imaging volume if the source 12 is rotated. In yet another embodiment both the source 12 and the detector 22 may remain stationary. In embodiments in which the source 12 and/or detector 22 are rotated, the rotational subsystem 26 may include a gantry. Thus, the system controller 24 It may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation 12 may be controlled by an X-ray controller 30 disposed within the system controller 24. Particularly, the X-ray controller 30 is configured to provide power and timing signals to the X-ray source 12.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 typically is coupled to or incorporates the system controller 24. The data collected by the data acquisition system 34 may be transmitted to the computer 36 for subsequent processing and reconstruction, or stored directly to memory 38. The computer 36 may comprise or communicate with a memory 38 that can store data processed by the computer 36 or data to be processed by the computer 36. It should be understood that any type of memory configured to store a large amount of data might be utilized by such an exemplary system 10. Moreover, the memory 38 may be located at the acquisition system or may include remote components, such as network accessible memory media, for storing data, processing parameters, and/or routines for implementing the techniques described below.

The computer 36 may also be adapted to control features such as scanning operations and data acquisition that may be enabled by the system controller 24. Furthermore, the computer 36 may be configured to receive commands and scanning parameters from an operator via an operator workstation 40, which is typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed images. Additionally, the scanned image may also be printed by a printer 44, which may be coupled to the operator workstation 40. The display 42 and printer 44 may also be connected to the computer 36, either directly or via the operator workstation 40. The operator workstation 40 may also be coupled to a picture archiving and communications system (PACS) 46. It should be noted that PACS 46 might be coupled to a remote system 48, such as radiology department information system (RIS), hospital information system (HIS) or to an internal or external network, so that others at different locations may gain access to the image data.

It should be further noted that the computer 36 and operator workstation 40 may be coupled to other output devices, which may include standard or special purpose computers and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, a virtual private network or the like.

Figure 2:
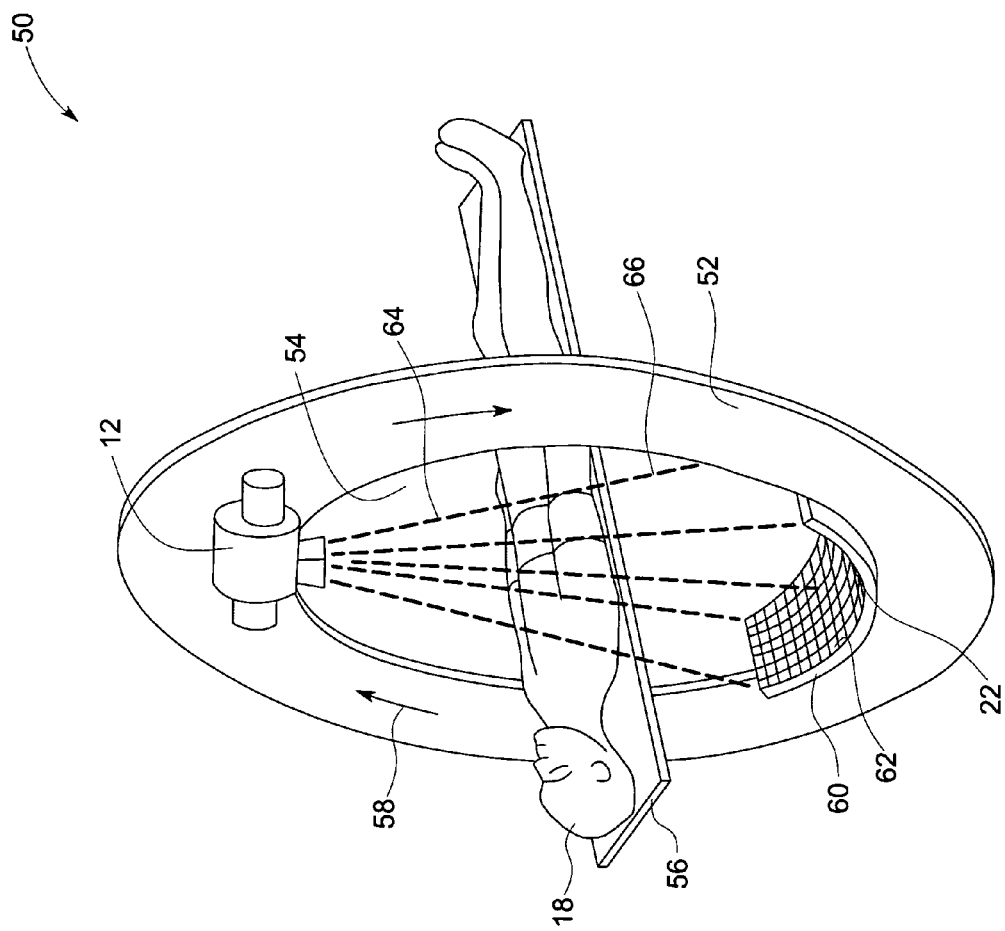
FIG. 2 is a block diagram of a physical implementation of the CT system of FIG. 1.

As noted above, an exemplary imaging system utilized in a present embodiment may be a CT scanning system 50, as depicted in greater detail in FIG. 2. The CT scanning system 50 may be a multi-slice CT (MSCT) system that offers a wide axial coverage, high rotational speed of the gantry, and high spatial resolution. Alternately, the CT scanning system 50 may be a volumetric CT (VCT) system utilizing a cone-beam geometry and an area detector to allow the imaging of a volume, such as an entire internal organ of a subject, at high or low gantry rotational speeds. The CT scanning system 50 is illustrated with a gantry 52 that has an aperture 54 through which a patient 18 may be moved. A patient table 56 may be positioned in the aperture 54 of the gantry 52 to facilitate movement of the patient 18, typically via linear displacement of the table 56 by the linear positioning subsystem 28 (see FIG. 1). The gantry 52 is illustrated with the source of radiation 12, such as an X-ray tube that emits X-ray radiation from a focal point. For cardiac imaging, the stream of radiation is directed towards a cross section of the patient 18 including the heart.

In typical operation, the X-ray source 12 projects an X-ray beam 64 from the focal point and toward detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 52 is rotated around the subject of interest in a direction 58 so that a plurality of radiographic views may be collected by the computer 36 (see FIG. 1). Furthermore, in accordance with exemplary aspects of the present technique, the detector array 22 may include a plurality of detector modules 60. The detector 22 may be assembled by tiling a plurality of detector modules 60 with gaps 62 between the detector modules 62 to allow for some manufacturing tolerance on the widths of the detector modules 60.

Thus, as the X-ray source 12 and the detector 22 rotate, the detector 22 collects data related to attenuated X-ray beams 66. Data collected from the detector 22 then undergoes preprocessing and calibration to condition the data to represent the line integrals of the attenuation coefficients of the scanned objects. The processed data, commonly called projections, may then be filtered and backprojected to generate an image of the scanned area. An image may be reconstructed, in certain modes, using projection data for less or more than 360 degrees of rotation of the gantry 52.

Figure 3:
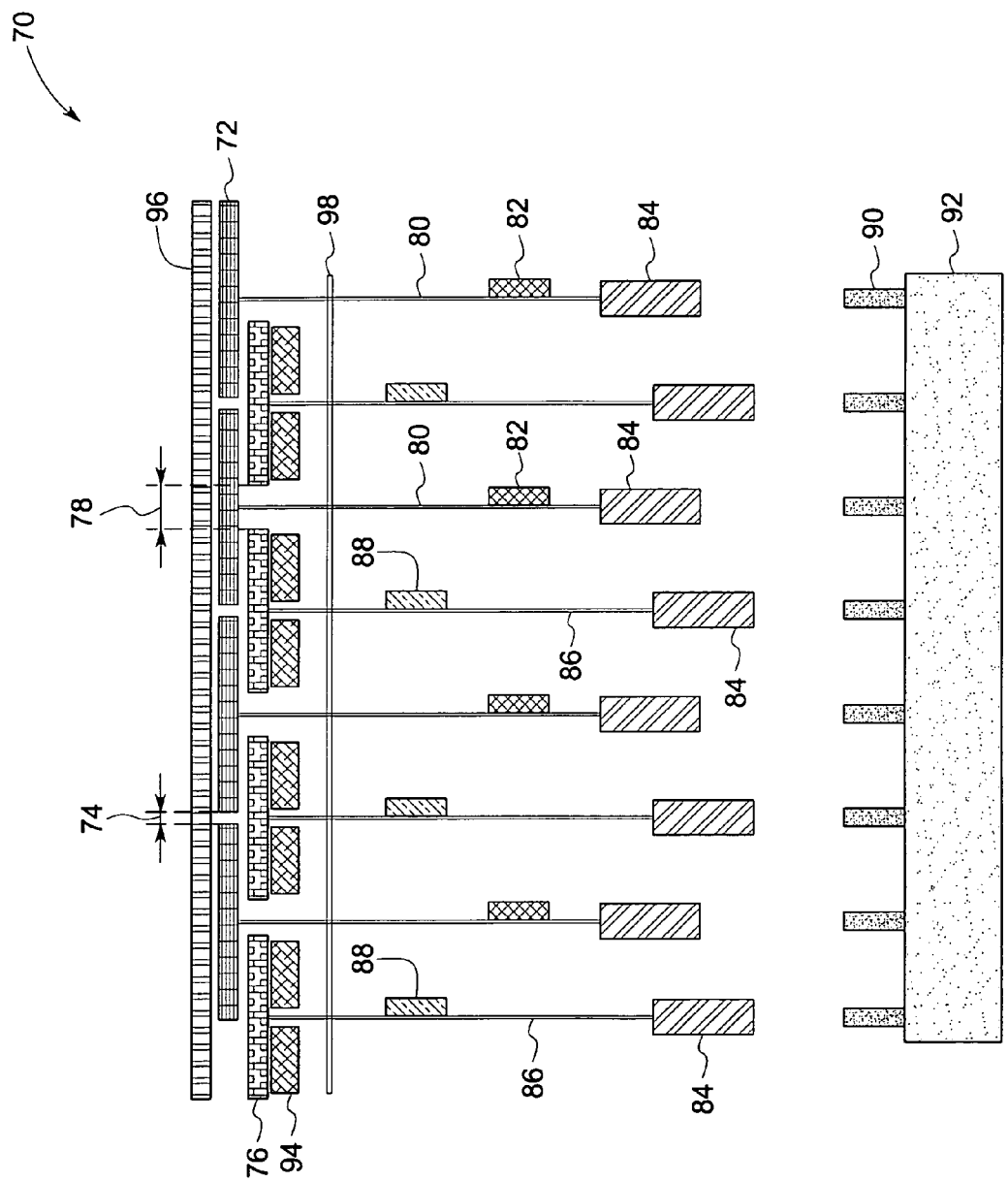
FIG. 3 is a cross-sectional side view of an exemplary tileable layered detector for use in the system illustrated in FIG. 1, in accordance with aspects of the present technique.

Turning now to FIG. 3, a cross-sectional side view 70 of an exemplary detector assembly for use in the system depicted in FIG. 1 is illustrated. In a presently contemplated configuration, the detector assembly 70 is shown as including a first detector layer 72 having a top side and a bottom side. The first detector layer 72 may be arranged such that the top side of the first detector layer 72 is arranged to receive radiation before the bottom side of the first detector layer 72. It may also be noted that the first detector layer 72 may include a scintillator or direct conversion sensor material, in certain embodiments. More particularly, the scintillator may include a wide variety of scintillators, such as, but not limited to, gadolinium oxysulfide (GOS) or cesium iodide (CsI) or yttrium oxide ($Y_2O_3$). Further, the direct conversion material may include semiconductors such as, but not limited to, silicon, gallium arsenide, mercury iodide ($Hg_2I$), cadmium telluride (CdTe) or cadmium zinc telluride (CZT).

Moreover, the first detector layer 72 may be configured to operate in a photon counting mode with energy binning. In addition, the first detector layer 72 may be configured to operate in an integration mode. Alternatively, the first detector layer 76 may be configured to switch between the photon counting mode and the integration mode.

Also, in one embodiment, the thickness of the first detector layer 72 may be selected to have a relationship to the amount of desired flux to be transmitted through the first detector layer 72 to a second detector layer. Accordingly, the thickness of the first detector layer 72 may be in a range from about 0.1 to 1 mm. For example, for low atomic number sensor materials like silicon, the attenuation may be low and the thickness of the first detector layer 72 may accordingly be in a range from about 0.1 mm to about 10 mm. In a similar fashion, for high atomic number sensor materials like GOS, CsI, $Hg_2I$, $Y_2O_3$, the thickness of the first detector layer 72 may be in a range from about 0.1 mm to about 2 mm. These thin first detector layers may be formed by a deposition process, screen printing or by bonding a monolithic sensor material.

In accordance with aspects of the present technique, the first detector layer 72 may also include a plurality of first coupling gaps 74. As previously noted with reference to FIG. 2, the detector 22 (see FIG. 2) may include gaps 62 (see FIG. 2) between the plurality of detector modules 60 (see FIG. 2), where the gaps 62 are configured to allow for some manufacturing tolerance on the widths of the detector modules 60. Accordingly, in a presently contemplated configuration, these first coupling gaps 74 may be configured to accommodate the manufacturing tolerance of the width of the detector module. The presence of these first coupling gaps 74 advantageously facilitates relatively easy assembly of the detector modules into the detector. More particularly, during assembly, the detector modules may be easily placed into the detector without physical interference at the boundaries of the detector modules. Furthermore, these first coupling gaps 74 may be configured to facilitate coupling between the top side and the bottom side of the first detector layer 72. For example, the first coupling gaps 74 may be configured to aid in routing of electronics configured to electrically couple the top side and the bottom side of the first detector layer 72. Furthermore, the plurality of first coupling gaps 74 may have a width in a range from about 5 microns to about 50 microns, in certain embodiments.

Additionally, in accordance with further aspects of the present technique, the detector assembly 70 may include a second detector layer 76 having a corresponding top side and a bottom side. In one embodiment, the second detector layer 76 may be disposed adjacent to the bottom side of the first detector layer 72. Further, the second detector layer 76 may be arranged such that the top side of the second detector layer 76 is arranged to receive radiation before the bottom side of the second detector layer 76. Also, the second detector layer 76 may include either scintillators or direct conversion sensor materials as previously described with reference to the first detector layer 72. Additionally, the second detector layer 76 may be configured to operate in a photon counting mode or an integration mode, as noted with reference to the first detector layer 72.

As will be appreciated, a portion of the incident flux may be transmitted through the first detector layer 72 to the second detector layer 76. The second detector layer 76 may therefore be configured to have a thickness sufficient to prevent the flux incident on the second detector layer 76 from being transmitted through the thickness of the second detector layer 76. Accordingly, the second detector layer 76 may have a thickness in a range from about 3 mm to about 5 mm. It may be noted that a plurality of pixels in the second detector layer 76 may be disposed at an offset with respect to a plurality of pixels in the first detector layer 72. This offset arrangement of pixels in each of the first detector layer 72 and the second detector layer 76 advantageously results in higher resolution. More particularly, in regards to spatial resolution, sampling of the incident radiation may be optimal when the pixels of the first detector layer 72 are superimposed with respect to that of the second detector layer 76 by an offset of ½ of the pixel pitch dimension. In certain embodiments, the plurality of pixels in the second detector layer 76 may be disposed at an offset of about one half of the pixel pitch with respect to a plurality of pixels in the first detector layer 72. The layout of the pixel array in the second detector layer 76 may be a uniform array with pixel position gaps corresponding to the physical gaps between detector modules and the uniform array is disposed with an offset of ½ of the pixel spacing.

Moreover, in accordance with further aspects of the present technique, the second detector layer 76 may include a plurality of second coupling gaps 78. These second coupling gaps 78 may be configured to facilitate coupling the first detector layer 72 to associated electronics, such as read out electronics, for example. In one embodiment, the second coupling gaps 78 may be configured to aid in routing of electronics configured to electrically couple the first detector layer 72 to associated electronics. It may be noted that the plurality of second coupling gaps 78 may be configured to have a width that is substantially larger than the width of the plurality of first coupling gaps 74 as the plurality of second coupling gaps 78 may be configured to facilitate passage of the interconnect structures from the first detector layer 72, while the plurality of first coupling gaps 74 may be configured to accommodate mechanical tolerance during manufacture and assembly. In a presently contemplated configuration, the plurality of second coupling gaps 78 may have a width in a range from about 20 microns to about 300 microns. In contrast, the plurality of first coupling gaps 74 may have a width in a range from about 5 microns to about 50 microns, as previously noted.

In the presently contemplated configuration illustrated in FIG. 3, the detector assembly 70 may also include one or more first interconnect structures 80. Each of the one or more first interconnect structures 80 may be configured to facilitate transfer of a first set of image data acquired via the first detector layer 72 to backplane electronics 92, for instance. In one embodiment, the first interconnect structures 80 may include a flexible interconnect structure, where the flexible interconnect structure includes one or more copper traces disposed on a polyimide film. One end of the first interconnect structures 80 may be operationally coupled to the first detector layer 72. More particularly, one end of the first interconnect structure 80 may be configured to be in operative association with the bottom side of the first detector layer 72. The other end of the first interconnect structures 80 may be coupled to a first set of electronics 82, where the first set of electronics 82 may include readout electronics.

Moreover, as noted hereinabove, the detector assembly 70 may also include a plurality of first set of electronics 82 corresponding to the plurality of first interconnect structures 80. In one embodiment, each of the plurality of first set of electronics 82 may be disposed adjacent to a respective first interconnect structure 80. Additionally, each of the plurality of first set of electronics 82 may be operatively coupled to the respective first interconnect structure 80 and configured to process the first set of image data. For example, the first set of electronics 82 may include Application Specific Integrated Circuits (ASICs), Floating Point Gate Arrays (FPGAs), Digital Signal Processing (DSP) chips, passive signal conditioning circuits, or power regulation circuits. As will be appreciated, the first set of image data may include analog signals acquired via the first detector layer 72. The ASICs 82 may be configured to convert the analog signals of the first set of image data to corresponding digital signals. These digitals signals representative of the first set of image data may then be communicated to a host computer via the backplane electronics 92, for instance.

Further, in certain embodiments, the digital readout data may be connected to the backplane electronics 92 via connectors 84. Accordingly, the connectors 84 may be configured to operatively couple the first interconnect structures 80 to the backplane electronics 92. In one embodiment, the connectors 84 may include make-break connectors, for example.

With continuing reference to FIG. 3, the detector assembly 70 may also include one or more second interconnect structures 86. As previously noted with reference to the first interconnect structures 80, each of the one or more second interconnect structures 86 may be configured to facilitate transfer of a second set of image data acquired via the second detector layer 76 to the backplane electronics 92, for instance. In certain embodiments, the second interconnect structures 86 may include flexible interconnect structures, where the flexible interconnect structures include one or more copper traces disposed on a polyimide film. One end of the second interconnect structures 86 may be operationally coupled to the second detector layer 76. Furthermore, as described with reference to the first interconnect structure 80, one end of the second interconnect structures 86 may be configured to be in operative association with the bottom side of the second detector layer 76. Additionally, the other end of the second interconnect structures 86 may be coupled to a second set of electronics 88, where the second set of electronics 88 may include readout electronics.

Also, the detector assembly 70 may include a plurality of second set of electronics 88, as noted hereinabove. The second set of electronics 88 may be disposed adjacent to the second interconnect structures 86. As illustrated in the embodiment of FIG. 3, each of the plurality of second set of electronics 88 may be disposed adjacent to a respective second interconnect structure 86. Furthermore, each of the plurality of second set of electronics 88 may be operatively coupled to the respective second interconnect structure 86 and configured to process the second set of image data. The second set of electronics 88 may include ASICs, where the ASICs may be configured to convert the analog signals in the second set of image data acquired via the second detector layer 76 to corresponding digital signals. Additionally, the second set of electronics may also include FPGAs, DSPs, signal conditioning passive components, or power regulation circuits. The digital signals may subsequently be communicated to a host computer via the backplane electronics 92, for instance. Reference numeral 90 is representative of a mating connector plug for the connector 84.

In accordance with aspects of the present technique, the detector assembly 70 may also include an exemplary support structure 94 configured to provide support to the first detector layer 72 and the second detector layer 76. The support structure 94 will be described in greater detail with reference to FIG. 5.

The detector assembly 70 may also include an anti-scatter collimator 96. In certain embodiments, the anti-scatter collimator 96 may be disposed adjacent to the top side of the first detector layer 72. As will be appreciated, the anti-scatter collimator 96 may be configured to selectively attenuate incident radiation that is at an angle with respect to surface-normal direction. In certain embodiments, the anti-scatter collimator 96 may include an arrangement of one or more thin attenuating lamina plates or cells located at pixel boundaries. This arrangement of lamina plates may be configured to selectively pass X-rays that travel at normal incidence to the detector plane, while selectively attenuating the X-rays that travel at a non-normal incidence to the detector plane.

It may be noted that the first set of electronics 82 and the second set of electronics 88 may be susceptible to damage when exposed to X-ray radiation. In order to prevent any damage to the first set of electronics 82 and the second set of electronics 88, the detector assembly 70 may include an X-ray shield 98. In a presently contemplated configuration, the X-ray shield 98 may be disposed adjacent to the support structure 94 such that the X-ray shield 98 is positioned between the support structure 94 and the first set of electronics 82 and the second set of electronics 88.

By implementing the detector assembly 70 as described hereinabove, a detector assembly 70 with multiple layers may be constructed, where the detector assembly 70 is configured to have a plurality of coupling gaps to allow for passage of electronic packaging materials. Additionally, loss of information due to missing pixels in the plurality of second coupling gaps 78 may be compensated for by interpolation within the second set of image data or by combining image data from the multiple layers, as will be described in greater detail with reference to FIGS. 6-9. For example, if the first detector layer 72 is saturated due to sensitivity to high flux rate, then the second set of image data may be used to substitute for the first set of image data. Additionally, if the first detector layer 72 includes an energy sensitive detector, such as a photon counting detector with energy binning, then the first set of image data may advantageously be overlaid or otherwise combined with the second set of image data to generate an image with combined material and density information. Furthermore, data from the first detector layer 72 and the second detector layer 76 may be combined to generate material discrimination information by utilizing the different energy selectivity of the first and second detector layers 72, 76. Such energy selectivity may be caused due to the beam hardening of the spectrum in the second detector layer 76 due to the attenuation of the first detector layer 72. Additionally, the method may include applying a material discrimination algorithm to the combined image data by utilizing the different spectral sensitivity and/or photon counting capabilities of the first and second detector layers 72, 76.

Figure 4:
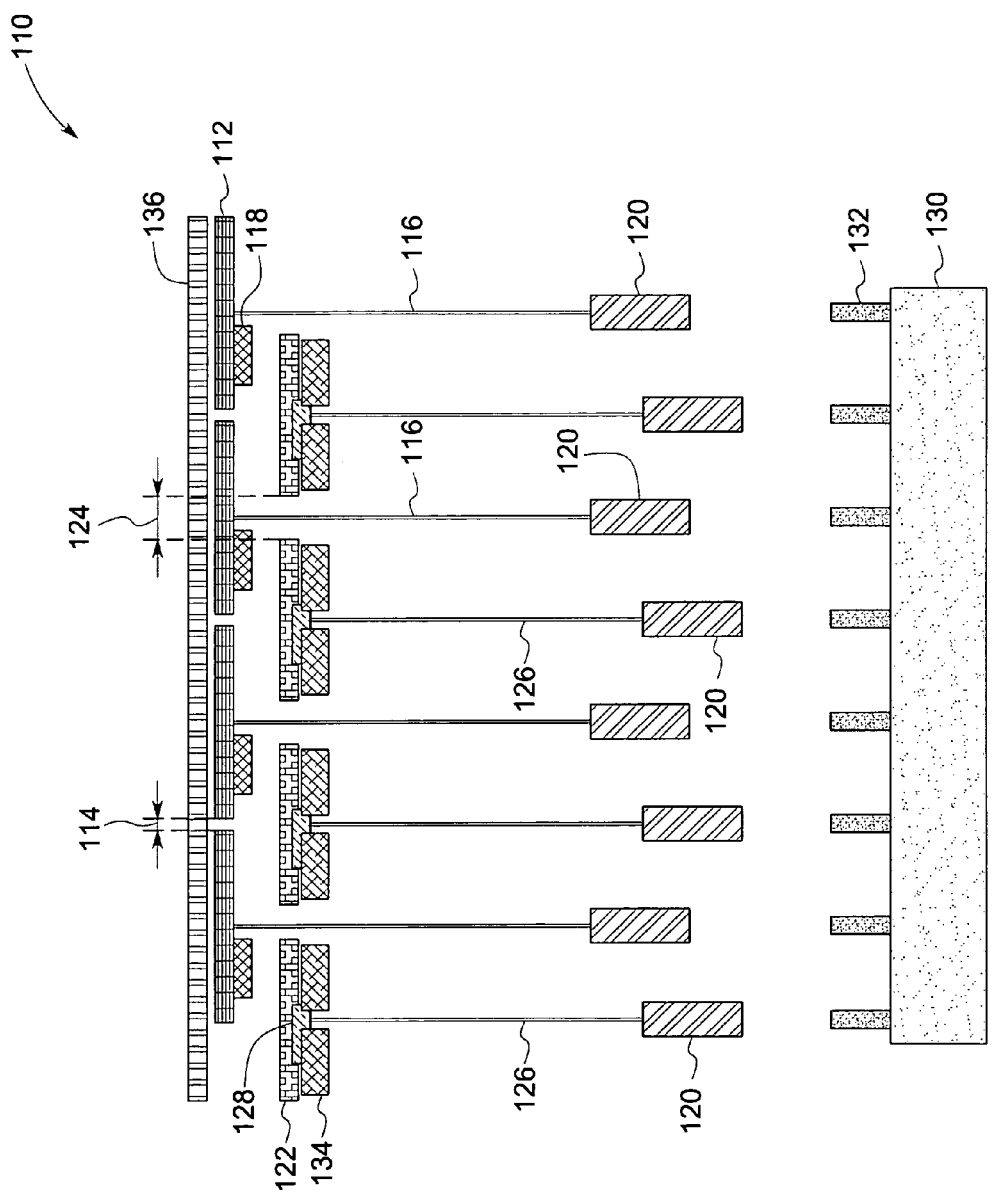
FIG. 4 is a cross-sectional side view of another exemplary tileable layered detector for use in the system illustrated in FIG. 1, in accordance with aspects of the present technique.

Referring now to FIG. 4, a cross-sectional side view 110 of another exemplary tileable layered detector assembly for use in the system 10 (see FIG. 1) is illustrated. In one embodiment, the detector assembly 110 may include at least one first detector module. According to aspects of the present technique, the first detector module may include a first detector layer 112 having a top side and a bottom side. Additionally, the first detector layer 112 may also include a plurality of first coupling gaps 114. As previously noted with reference to FIG. 3, the plurality of first coupling gaps 114 may be configured to accommodate mechanical tolerance during manufacture and assembly. Additionally, the plurality of first coupling gaps 114 may be configured to facilitate coupling the top side and the bottom side of the first detector layer 112.

The first detector module 112 may also include a first interconnect structure 116 configured to facilitate transfer of a first set of image data acquired via the first detector layer 112 to backplane electronics 130. As previously described with reference to FIG. 3, the first interconnect structure 116 may include a flexible interconnect layer having a plurality of copper traces disposed on a polyimide film. In addition, the first detector module may include a first set of electronics 118 that may be configured to process the first set of image data acquired via the first detector layer 112. In certain embodiments, the first set of electronics 118 may include ASIC, FPGAs, DSPs, signal conditioning passive components, or power regulation circuits configured to convert analog image data into corresponding digital image data, which may then be transferred to the backplane electronics 130. Connectors 120 that may be coupled to the first interconnect structures 116 may be employed to facilitate operatively coupling the first interconnect structures 116 to the backplane electronics 130.

In accordance with further aspects of the present technique, the detector assembly 110 may also include a second detector module. This second detector module may include a second detector layer 122, a second interconnect structure 126 and a second set of electronics 128. The second detector layer 122 may have a corresponding top side and a bottom side and may be configured to acquire a second set of image data. In addition, the second detector layer 122 may also include a plurality of second coupling gaps 124 that may be configured to facilitate passage of the first interconnect structure 116 from the first detector layer 112 to the backplane electronics 130. As previously noted, the plurality of second coupling gaps 124 may be configured to be substantially larger than the plurality of first coupling gaps 114.

Moreover, the second interconnect structure 126 may be configured to facilitate transfer of the second set of image data acquired via the second detector layer 122 to backplane electronics 130. Further, the second set of electronics 128 may be configured to process the second set of image data acquired via the second detector layer 122. In certain embodiments, the second set of electronics 128 may include ASICs, FPGAs, DSPs, signal conditioning passive components, or power regulation circuits configured to convert analog image data into corresponding digital image data, which may then be transferred to the backplane electronics 130. Connectors 120 that are coupled to the second interconnect structures 126 may be employed to facilitate operatively coupling the second interconnect structures 126 to the backplane electronics 130. Reference numeral 132 is representative of a mating connector plug for the connector 120.

In accordance with aspects of the present technique, a plurality of first detector modules and a plurality of second detector modules may be disposed on a support structure 134. As previously noted, the support structure 134 may include a plurality of slots that may be configured to facilitate passage of the plurality of first detector modules and the plurality of second detector modules. Accordingly, the plurality of first detector modules and the second detector modules may be aligned and mechanically secured to the support structure 134 following an alignment process. In one embodiment, such alignment may be performed with optical pick-and-place equipment, for example, that will register the pixel positions of different pixels into a uniform array and the array to a fiducial marking on the support structure 134. It may be noted that other equipment known in the art, such as, but not limited to, fixtures that reference to the sidewall of the module, may also be employed to perform the alignment step. Also, in a presently contemplated configuration, the detector assembly 110 may include an anti-scatter collimator 136 disposed adjacent to the first detector layer 112, where the anti-scatter collimator 136 may be configured to include attenuating lamina, as previously described. Furthermore, the anti-scatter collimator 136 may also be aligned and fixed to the support structure 134.

As previously noted with reference to FIG. 3, an X-ray shield, such as the X-ray shield 98 (see FIG. 3), may be disposed such that the plurality of ASICs are protected from potentially damaging X-ray radiation. In the embodiment of the tileable layered detector assembly 110 illustrated in FIG. 4, an X-ray shield (not shown) may be disposed adjacent to each of the ASICs. In other words, in certain embodiments, an X-ray shield may be disposed on top of the first set of electronics 118. Additionally, an X-ray shield may also be disposed on top of the second set of electronics 128.

As will be appreciated, various applications such as medical and industrial imaging, biomedical non-invasive diagnostics, non-destructive testing (NDT) and non-destructive evaluation (NDE) of materials, security and baggage scanning, may entail the use of detector assemblies that encompass large areas. For example, in the field of medical diagnostics, such as, but not limited to ultrasound and mammography, it may be desirable to employ detector assemblies that encompass large areas. For instance, in order to obtain enhanced image quality it may be desirable to employ large area detectors that are capable of covering a relatively large portion of the anatomy in a single gantry rotation. In particular, cardiac images with enhanced image quality may be obtained via the use of such large area detectors as the entire image data set may be acquired in a relatively short period of time especially when the heart is in a slow moving phase. In a similar fashion, security applications such as baggage scanning may entail use of detector assemblies that encompass large areas. In accordance with exemplary aspects of the present technique, a detector assembly that encompasses a large area is presented. It may be noted that the term "large area" detector assembly is used to represent a detector assembly that has a square area in a range from about 10 $cm^2$ to about 50 $cm^2$.

Although the embodiments of the tileable layered detectors depicted in FIGS. 3-4 are illustrated as having a planar configuration, it may be appreciated that the tileable layered detectors may also be configured to exhibit an arc shape or a partial arc shape. In certain embodiments, the arc-shaped detector may be configured to have a width of about 75 cm to about 1.5 meters.

The large area detector assembly may be formed by tiling a plurality of first detector modules and a plurality of second detector modules. As used herein, the terms "tiling" and "tileable" refer to placing detector modules adjacent to one another or otherwise arranged in a pattern to form an array in a manner analogous to floor tiles. In one embodiment, a second detector module may be disposed adjacent to a first detector module to form a detector sub-group. Subsequently, a plurality of such detector sub-groups may be tiled to form a large area detector assembly. Alternatively, a plurality of first detector modules may be arranged to form a first detector sub-group. Similarly, a second detector sub-group may be formed by arranging a plurality of second detector modules. A large area detector assembly may then be formed by tiling a plurality of first detector sub-groups and a plurality of second detector sub-groups. As described hereinabove, the plurality of first detector modules and the plurality of second detector modules may be aligned and mechanically fixed on the support structure 134, while the plurality of slots on the support structure 134 may be utilized to facilitate the passage of these detector modules.

In the embodiment illustrated in FIG. 4, the detector assembly 110 is shown as including one backplane 130. In other words, a plurality of first detector modules and a plurality of second detector modules may be coupled to a single larger backplane, such as the backplane 130, for example, as depicted in the embodiment of FIG. 4. However, in certain other embodiments, the detector assembly 110 may include more than one backplane. More particularly, the detector assembly 110 may include a first backplane (not shown) that is operatively coupled to the plurality of first detector modules. Similarly, a second backplane (not shown) may be operatively coupled to the plurality of second detector modules in the detector assembly 110.

By implementing the detector assembly 110 as described hereinabove, a large area detector assembly may be constructed. Additionally, in the detector assembly 110 respective sets of electronics may be integrated into the corresponding detector modules. More particularly, the first set of electronics 118 may be integrated with the corresponding first detector layer 112, while the second set of electronics 128 may be integrated with the corresponding second detector layer 122. Consequently, the respective interconnect structures, such as the first interconnect structures 116 and the second interconnect structures 126 may be configured to facilitate only digital communication and power functionality. The interconnect structures 116, 126 may thereby be configured to have a relatively small size, consequently allowing relatively smaller slots in the support structure 134.

Figure 5:
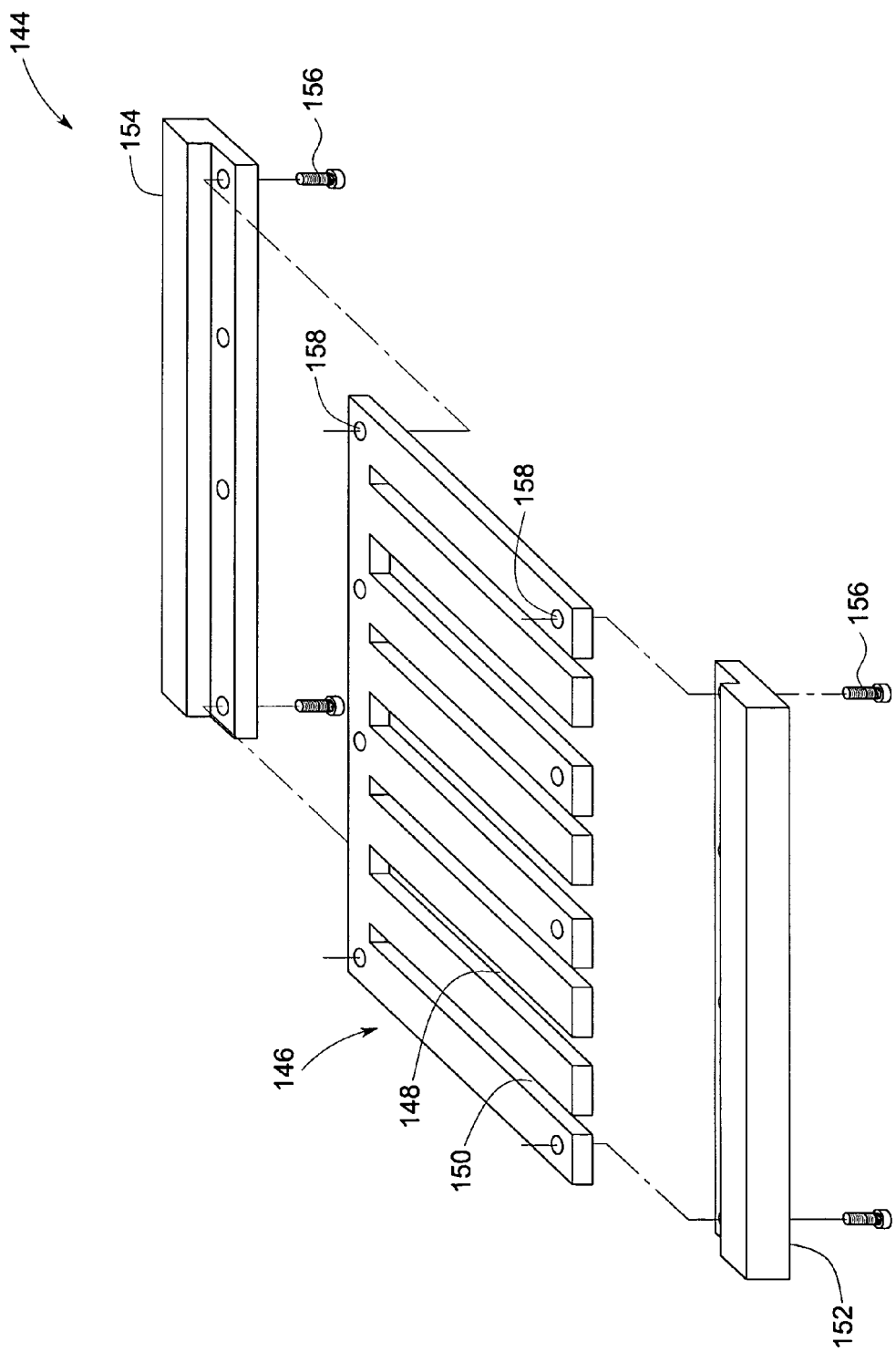
FIG. 5 is an exploded view of a support structure assembly for use in the tileable layered detectors illustrated in FIGS. 3-4, in accordance with aspects of the present technique.

Turning now to FIG. 5, an exploded view 144 of an exemplary support assembly for use in the detector assemblies of FIGS. 3-4 is illustrated. In the illustrated embodiment, the support assembly 144 is shown as including a support structure 146. In accordance with aspects of the present technique, the support structure 146 may be configured to keeping a plurality of first detector modules and a plurality of second detector modules in place by restraining one or more degrees of freedom. In one embodiment, the support structure 146 may include stainless steel, low-expansion iron/nickel alloys such as $FeNi_{36}$ or $FeNi_{42}$, aluminum, engineering plastics, such as ULTEM® polyetherimide, LEXAN® polycarbonate, aluminum silicon carbide (AlSiC), or a laminate or metal matrix composite (MMC) material.

In a presently contemplated configuration, the support structure 146 may include a plurality of slots. For example, the support structure 146 may include a plurality of first slots 148 configured to facilitate passage of the first interconnect structures, such as the first interconnect structures 80 (see FIG. 3), for example. It may be noted that the plurality of first slots 148 may have a width that is configured to accommodate the thickness of the first interconnect structures 80. Accordingly, the plurality of first slots 148 may have a width in a range from about 0.5 mm to about 5 mm.

Moreover, the support structure 146 may also include a plurality of second slots 150 configured to allow the second interconnect structures, such as the second interconnect structures 86 (see FIG. 3), to pass through. As noted hereinabove, the plurality of second slots 150 may have a width that is dependent upon the thickness of the plurality of second interconnect structures 86. Thus, the plurality of second slots 150 may have a width in a range from about 0.5 mm to about 5 mm. It may be noted that in certain embodiments, the width of the plurality of second slots 150 may be the same as the width of the plurality of first slots 148. Alternatively, in certain other embodiments, the width of the plurality of second slots 150 may be different from the width of the plurality of first slots 148.

In accordance with further aspects of the present technique, each of the plurality of first slots 148 and second slots 150 on the support structure 146 may also be configured to accommodate passage of both the first interconnect structures and the second interconnect structures. Consequently, the plurality of slots may have a width in a range from about 0.5 mm to about 5 mm, in certain embodiments.

As described hereinabove, the plurality of first detector modules and the plurality of second detector modules may be aligned and mechanically secured to the support structure 146. It may also be noted that the plurality of first detector modules and the plurality of second detector modules may be thermally controlled by the support structure 146. Thermal control may be accomplished by securing heating elements and temperature sensing elements to the support structure 146. As will be appreciated, power to the heating elements may be controlled by comparing the temperature read by the temperature sensing elements to a preset reference point. In certain embodiments, a commercially available proportional-integral-derivative (PID) controller may be employed to facilitate thermally controlling the support structure 146.

As illustrated in FIG. 5, the support assembly 144 may also include one or more detector rails. As will be appreciated, the one or more detector rails may include a steel structure with precise alignment features configured to align the detector modules or sub-units within the intended geometry of the imaging system. In the embodiment illustrated in FIG. 5, the support assembly 144 is shown as including a first detector rail 152 and a second detector rail 154. The support structure 146 may be secured to the first detector rail 152 and the second detector rail 154 with the aid of one or more bolts 156 that may be configured to fit through a plurality of threaded holes 158 that may be disposed on the support structure 146. However, other forms of securing the support structure 146 to the one or more detector rails 152, 154 may also be employed. Additionally, an anti-scatter collimator (not shown), such as the anti-scatter collimator 96 (see FIG. 3), may be aligned and secured to the one or more detector rails 152, 154.

As described hereinabove, a layered, tileable detector assembly includes at least a first detector layer and a second detector layer. Accordingly, a first set of image data may be acquired via the first detector layer, while the second detector layer may be used to acquire a second set of image data. These sets of image data may then be employed to facilitate material decomposition and reconstruction of the acquired image data. In other words, the two sets of image data may be accordingly processed to generate a reconstructed image and material specific images.

Figure 6:
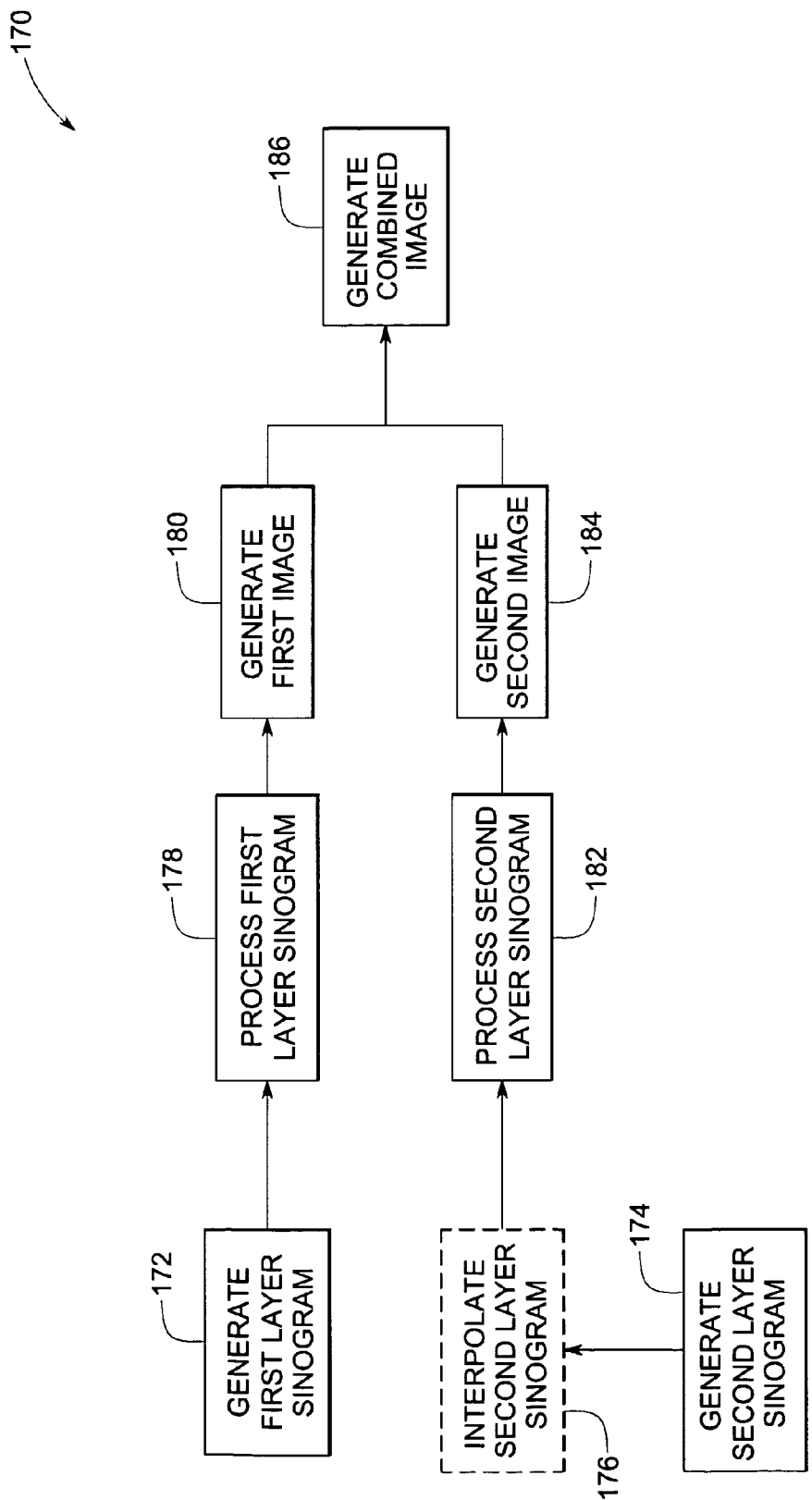
FIG. 6 is a flow chart depicting an exemplary method for imaging employing the tileable layered detectors illustrated in FIGS. 3-4, in accordance with aspects of the present technique.

FIG. 6 is a flow chart 170 depicting an exemplary method for imaging employing the tileable layered detector illustrated in FIGS. 3-4. In accordance with aspects of the present technique, a method for imaging using the exemplary tileable layered detector is presented. The method starts at step 172 where a first layer sinogram may be generated using a first set of image data acquired via a first detector layer in the detector assembly, such as the detector assemblies 70 (see FIG. 3), 110 (see FIG. 4). Similarly, step 174 may entail generation of a second layer sinogram using a second set of image data acquired via a second detector layer in the detector assembly.

As previously noted, the second detector layer is described as having a plurality of second coupling gaps configured to facilitate passage of a plurality of first interconnect structures. The presence of the plurality of second coupling gaps in the second detector layers may result in "missing" data in the second set of image data. More particularly, missing pixels in the plurality of second coupling gaps may result in loss of information in the second set of image data. Additionally, as previously described with reference to FIG. 4, an X-ray shield may be disposed on top of each of the first set of electronics 118 (see FIG. 4) and the second set of electronics 128 (see FIG. 4). The presence of the X-ray shield thereby results in degrading and/or blocking out of image data in the second layer sinogram. In one embodiment, loss of information may be circumvented by employing a relatively "thin" interconnect layer for the first interconnect structures that pass through the plurality of second coupling gaps. For example, the first interconnect structures may include thin, flexible, laminate electronics that have a thickness less than about 0.1 mm.

However, certain conditions may disallow use of such thin interconnect layers. In such situations, this loss of information in the second set of image data may be compensated by interpolating within the second set of image data across the plurality of second coupling gaps, in accordance with exemplary aspects of the present technique. Furthermore, the second detector layer being disposed further from the source of radiation than the first detector layer may have a different magnification within the imaging geometry. Accordingly, at step 176, the second set of image data may be interpolated to compensate for the missing data and difference in magnification, thereby resulting in a "complete" second set of image data registered to the first set of data. As will be appreciated, interpolation methods, such as, but not limited to, linear interpolation methods, polynomial interpolation, or cubic splines may be used to facilitate interpolating the second set of image data over the plurality of second coupling gaps in the second detector layer. It may also be noted in the case where the pixels in the first detector layer and the second detector layer are positioned with an offset of ½ pixel spacing, the interpolation step may result in the generation of a data set with interlaced sampling.

Figure 7:
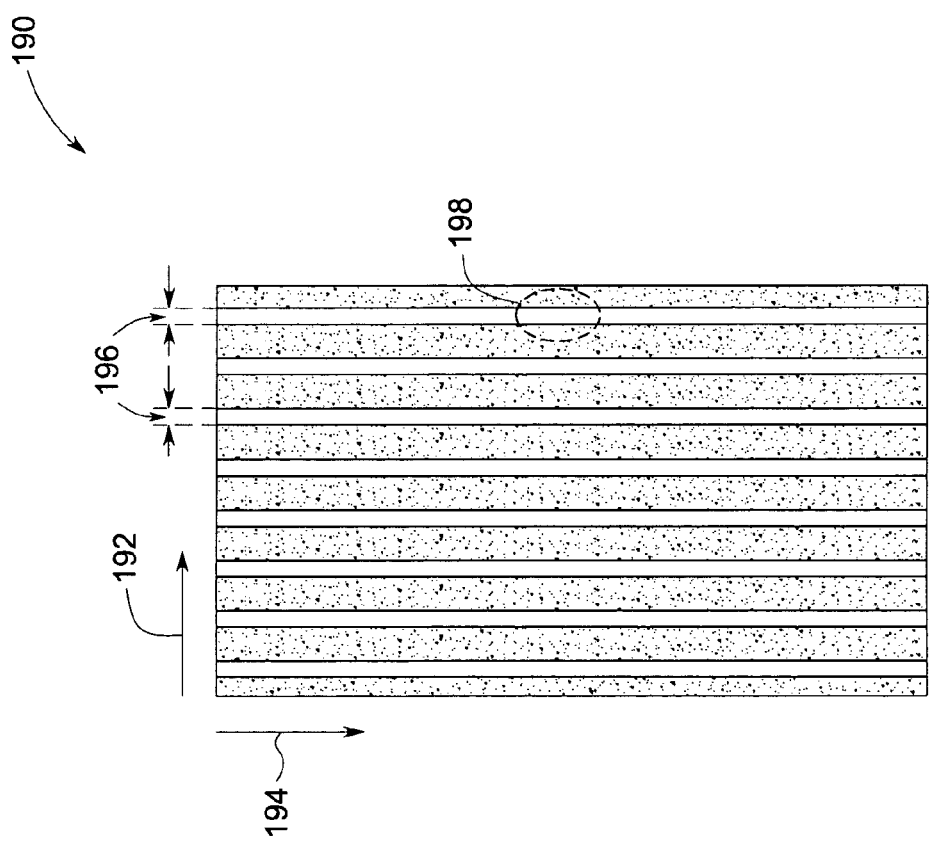
FIG. 7 is a diagrammatic illustration of a sinogram obtained via a second detector layer in the tileable layered detectors illustrated in FIGS. 3-4, in accordance with aspects of the present technique.

As described hereinabove, the second set of image data may be interpolated within to compensate for the missing data and magnification mismatch to generate a complete second set of image data that is registered to the first set of image data. For example, regions of missing data in the second set of image data may be interpolated via the use of neighboring image data. Alternatively, in certain other embodiments, the first sinogram generated at step 172 may be used to facilitate interpolation of the second sinogram to compensate for the missing data. FIG. 7 is a diagrammatic illustration of a sinogram 190 obtained via a second detector layer in the detectors illustrated in FIGS. 3-4. Reference numeral 192 is representative of a data channel number, while a view number is represented by reference numeral 194. Additionally, reference numeral 196 is indicative of missing data in certain columns in the second layer sinogram 190. The missing data in certain columns in the second layer sinogram 190 is due to the plurality of second coupling gaps in the second detector layer, as previously noted. Also, reference numeral 198 is representative of a portion of a column of missing data in the second layer sinogram 190.

Figure 8:
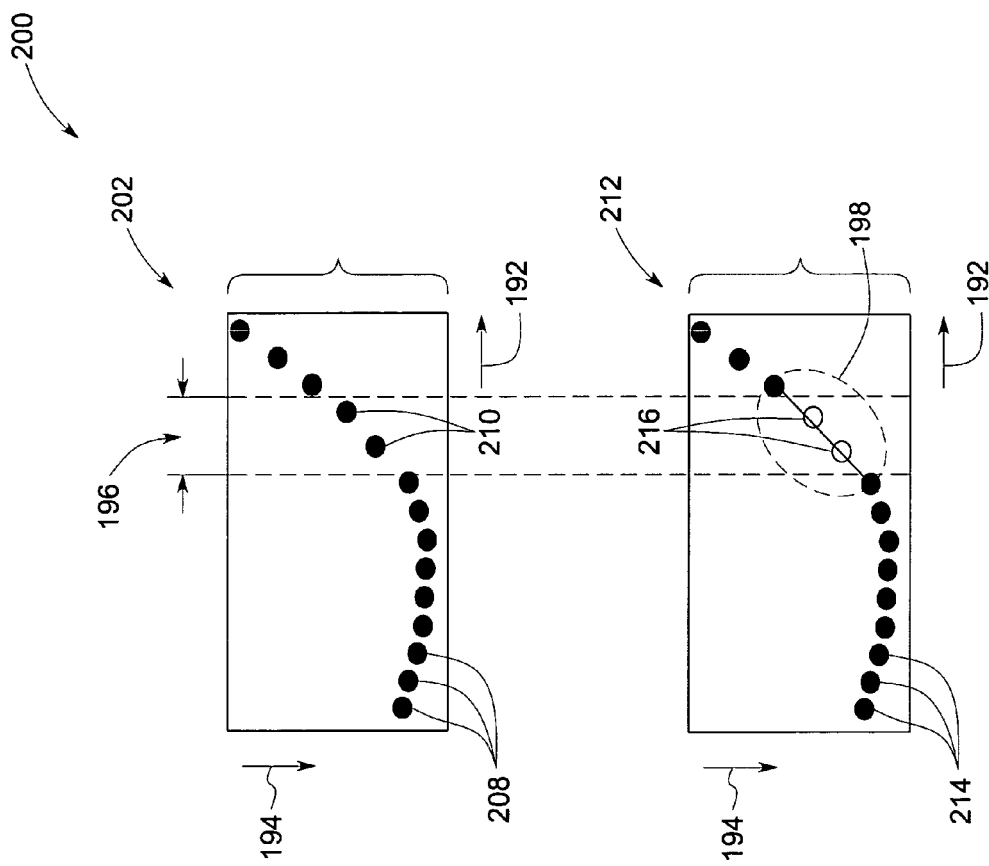
FIG. 8 is a schematic flow chart illustrating an exemplary process of sinogram interpolation, in accordance with aspects of the present technique.

As previously described, the missing data 196 in the second layer sinogram 190 may be compensated by interpolating the data within the second layer sinogram 190. FIG. 8 is a schematic flow chart 200 illustrating an exemplary process of sinogram interpolation. More particularly, in accordance with aspects of the present technique, a method for interpolating the second layer sinogram 190 (see FIG. 7) over a plurality of second coupling gaps in a second detector layer in a detector assembly, such as the detector assembly 70 (see FIG. 3), 110 (see FIG. 4), is presented. A portion of a first layer sinogram obtained via a first detector layer in the tileable layered detectors illustrated in FIGS. 3-4 is represented by reference numeral 202. Further, a data channel number is represented by reference numeral 192, while reference numeral 194 is indicative of a view number, as previously described in FIG. 7. Additionally, image data in the first layer sinogram 202 may be generally represented by reference numeral 208.

Referring further to FIG. 8, reference numeral 212 is indicative of a portion of a second layer sinogram, such as the second layer sinogram 190 (see FIG. 7), obtained via a second detector layer in the tileable layered detector illustrated in FIGS. 3-4. Also, reference numeral 214 is representative of image data in the second layer sinogram 212. As previously noted with reference to FIG. 7, reference numeral 196 is indicative of a column of missing data in the portion 212 of the second layer sinogram 190. Further, as noted hereinabove, for certain data channel positions in the second layer sinogram 212, there are no corresponding physical pixels due to the presence of the plurality of second coupling gaps in the second detector layer. Consequently, there is no one-to-one correspondence between the first layer sinogram 202 and the second layer sinogram 212, particularly in region 196. Reference numeral 210 is representative of image data in the first layer sinogram 202 that lies within the column 196. In accordance with aspects of the present technique, image data 210 in the first layer sinogram 202 may be utilized to facilitate interpolation of the missing data in the second layer sinogram 212. Consequent to the interpolation step 176 (see FIG. 6), missing data 216 in the column 196 in the second layer sinogram 212 may be obtained. In one embodiment, a linear interpolation method may be employed in the interpolation step 176, as previously noted.

Furthermore the mismatch in magnification may be such that the data points 214 in the second layer sinogram 214 do not correspond to the same projective rays of the data points 208 in the first layer sinogram 202. Accordingly, the interpolation may be performed on all the second layer data to produce an interpolated array of points corresponding to the same projective rays and the data points 208 in the first layer sinogram 202.

Alternatively, image data from other layers, such as the first detector layer, for example, may be combined with the second set of image data to recompense for the loss of information in the second set of image data. In other words, in one embodiment, image data acquired via the first detector layer (i.e., the first layer sinogram 202) may be combined with the second layer sinogram 212 to make up for the loss of information in the second set of image data. It may be appreciated that if the first detector layer is saturated due to sensitivity to high X-ray flux, the second set of image data may then be used to stand in for the first set of image data, and thereby permit reconstruction of the image data. For example, if the first detector layer includes an energy sensitive detector, then the corresponding first set of image data may be overlaid or otherwise combined with the second set of image data to facilitate forming an image with combined material and density information.

It may be noted that in certain embodiments, step 176 may be an optional step. As described hereinabove, use of relatively thin first interconnect structures that pass through the plurality of second coupling gaps aids in circumventing loss of information, thereby mitigating the need for an interpolation step.

With returning reference to FIG. 6, at step 178, the first layer sinogram generated at step 172 may be subject to a processing step to generate a processed first layer sinogram. In certain embodiments, the processing steps may include a filtering step, a scaling step, or both. It may be noted that other processing such as beam hardening correction or material decomposition may also be applied to the first layer sinogram. Subsequently, at step 180 a first set of image data may be reconstructed using the processed first layer sinogram obtained consequent to step 178. In certain embodiments, reconstruction algorithms, such as, but not limited to, filtered backprojection or iterative reconstruction may be employed to facilitate the reconstruction of the first set of image data. It may be noted that for cases where the first detector layer produces multi-energy bin data, multiple material images may be generated consequent to the processing and reconstruction steps.

Similarly, at step 182, the second layer sinogram generated at step 174 or step 176 may be processed to generate a processed second layer sinogram. The processed second layer sinogram may then be employed to reconstruct a second set of image data at step 184. Here again, reconstruction algorithms, such as, but not limited to, filtered backprojection and iterative reconstruction may be used to reconstruct the second image data set. Consequent to steps 180 and 184, a reconstructed first set of image data and a reconstructed second set of image data are generated. Following steps 180 and 184, the reconstructed first set of image data and the reconstructed second set of image data may be combined to generate a single combined image data set at step 186.

In the exemplary process 170 illustrated in FIG. 6, the first layer sinogram and the second layer sinogram are combined after reconstruction of a respective first set of image data and a second set of image data, which are then employed to generate a combined image data set, as described hereinabove. Alternatively, the first layer sinogram and the second layer sinogram may be combined prior to a reconstruction step as will be described with reference to FIG. 9.

By employing the method of imaging illustrated in FIG. 6, optimal combination of the first set of image data and the second set of image data may be achieved. For example, if the first detector layer includes an energy discrimination (ED) detector, while the second detector layer includes an energy integration (EI) detector, color overlay of material information on a density image may be accommodated.

Figure 9:
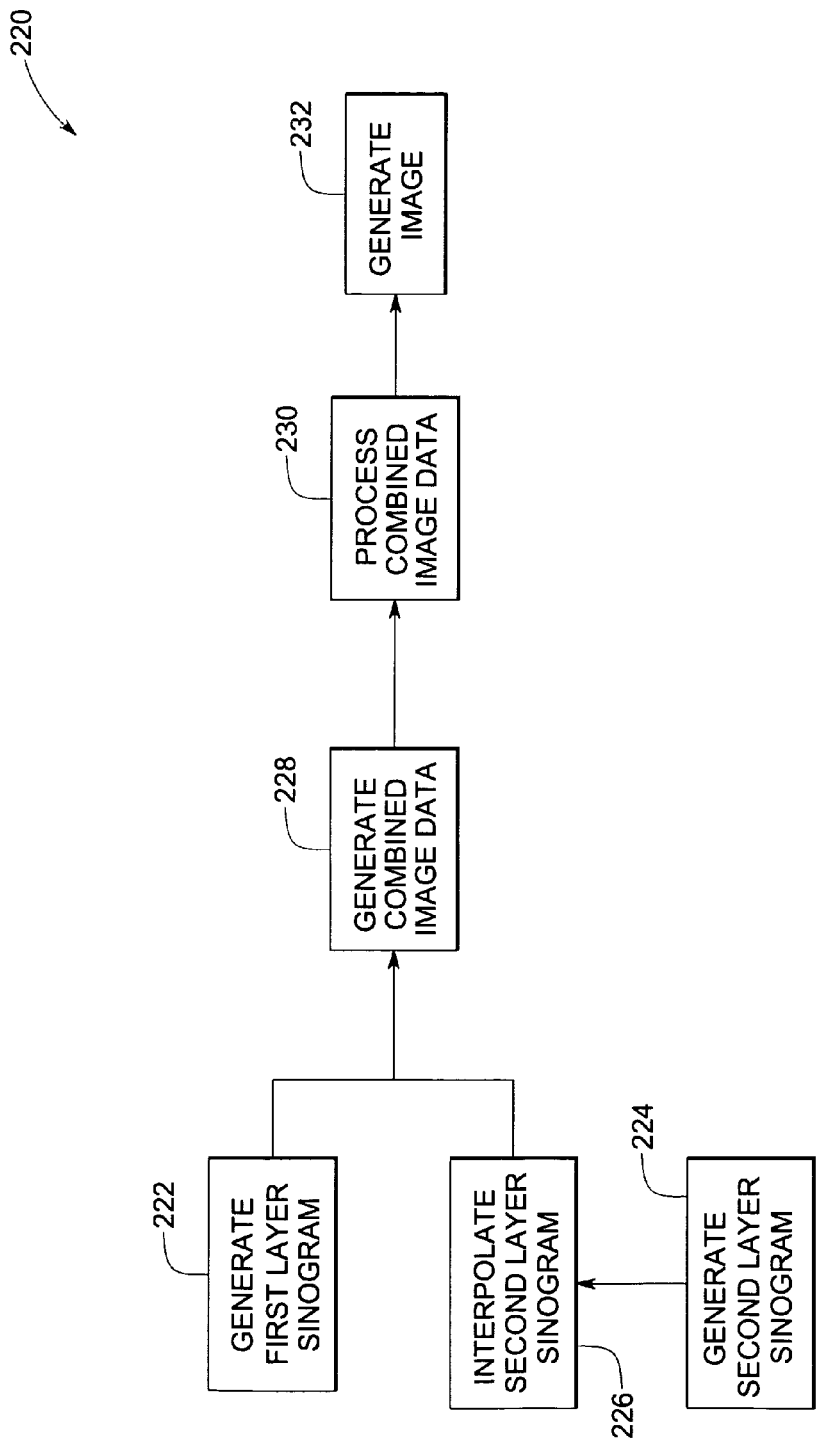
FIG. 9 is a flow chart depicting another exemplary method for imaging employing the tileable layered detectors illustrated in FIGS. 3-4, in accordance with aspects of the present technique.

Turning now to FIG. 9, a flow chart 220 depicting another exemplary method for imaging employing the tileable layered detectors illustrated in FIGS. 3-4 is illustrated. The method starts at step 222 where a first layer sinogram may be generated employing a first set of image data acquired via a first detector layer in the tileable layered detector. Similarly, a second layer sinogram may be generated employing a second set of image data acquired via a second detector layer in the tileable layered detector, at step 224. Subsequently, at step 226, the second layer sinogram may be interpolated to generate an interpolated second layer sinogram. As previously noted with reference to FIG. 6, the second layer sinogram may be interpolated within the second set of image data or may be combined with image data from the first detector layer, for example.

The first layer sinogram generated at step 222 and the interpolated second layer sinogram generated at step 226 may then be combined at step 228 to generate a combined image data set. Furthermore, the combined image data set may be processed at step 230 to generate a processed combined image data set. As previously noted, the processing step 230 may include a filtering step, a scaling step, or both. This processed combined image data set may then be utilized to generate an image at step 232. In one embodiment, the processing step 230 may include a material decomposition step that may be configured to generate data which may be reconstructed to indicate material basis or atomic number images in step 232.

By employing the method of imaging illustrated in FIG. 9, optimal combination of the first set of image data and the second set of image data of image to circumvent saturation associated with photon counting detectors may be achieved. For example, if the first detector layer includes a photon counting detector that is susceptible to corruption by saturation at a high flux rate, the second set of image data may be substituted for the first set of image data.

The detector assemblies 70 (see FIG. 3), 110 (see FIG. 4) are described as having a first detector layer and at least a second detector layer. These tileable layered detector assemblies may be used in the detector array 22 (see FIG. 1) included in an imaging system, such as the imaging system 10 (see FIG. 1). Such an imaging system may have material decomposition capability by leveraging the energy selectivity of the two layer data. In accordance with aspects of the present technique, it may be noted that these tileable layered detector assemblies may encompass the whole detector array. Alternatively, these tileable layered detector assemblies may be used to cover only a predetermined portion of the detector array 22. Accordingly, in certain embodiments, predetermined portions of the detector array 22 may include the exemplary tileable layered detector assembly 70, 110, while the other portions of the detector array 22 may include single layer detectors.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A detector assembly, comprising:
  a first detector layer having a top side and a bottom side, wherein the first detector layer comprises a plurality of first coupling gaps;
  a first interconnect structure operationally coupled to the first detector layer and configured to facilitate transfer of a first set of image data from the first detector layer to backplane electronics;
  a second detector layer having a top side and a bottom side and disposed adjacent the bottom side of the first detector layer, wherein the second detector layer comprises a plurality of second coupling gaps configured to facilitate passage of the first interconnect structure from the first detector layer to the backplane electronics; and a second interconnect structure operationally coupled to the second detector layer and configured to facilitate transfer of a second set of image data from the second detector layer to the backplane electronics.

2. The detector assembly of claim 1, wherein the plurality of first coupling gaps in the first detector layer is configured to permit coupling between the top and bottom sides of the first detector layer.

3. The detector assembly of claim 1, wherein the plurality of second coupling gaps in the second detector layer is substantially larger than the plurality of first coupling gaps in the first detector layer.

4. The detector assembly of claim 1, further comprising a support structure configured to support the first detector layer and the second detector layer.

5. The detector assembly of claim 1, further comprising a first set of electronics disposed adjacent the first interconnect structure, wherein the first set of electronics is in operative association with the first interconnect structure and configured to process the first set of image data.

6. The detector assembly of claim 1, further comprising a second set of electronics disposed adjacent the second interconnect structure, wherein the second set of electronics is in operative association with the second interconnect structure and configured to process the second set of image data.

7. The detector assembly of claim 1, further comprising an anti-scatter collimator disposed adjacent the top side of the first detector layer and configured to selectively attenuate incident radiation that is at an angle with respect to surface-normal direction.

8. The detector assembly of claim 1, further comprising an X-ray shield disposed adjacent the support structure and configured to shield electronics from X-ray radiation.

9. The detector assembly of claim 1, further comprising a plurality of connectors configured to couple each of the first interconnect structure and the second interconnect structure to the backplane electronics.

10. The detector assembly of claim 1, wherein each of the first interconnect structure and the second interconnect structure comprises a flexible circuit, and wherein the flexible circuit comprises one or more copper traces formed on a polyimide film.

11. The detector assembly of claim 1, wherein the top side of the first detector layer and the top side of the second detector layer are arranged to receive radiation before each respective bottom side of the first detector layer and the second detector layer.

12. The detector assembly of claim 1, wherein the first detector layer comprises a photon counting sensor or an integrating X-ray sensor and the second detector layer comprises a photon counting sensor or an integrating X-ray sensor.

13. The detector assembly of claim 1, wherein the detector assembly is constructed in a modular package, wherein the modular package is assembled with a plurality of modular packages to form a tiled detector assembly.

14. The detector assembly of claim 1, wherein the detector assembly comprises a planar detector, an arc-shaped detector, or a combination thereof.

15. A detector assembly, comprising:
a first detector module, comprising:
a first detector layer having a top side and a bottom side, wherein the first detector layer comprises a plurality of first coupling gaps;
a first interconnect structure operationally coupled to the first detector layer and configured to facilitate transfer of a first set of image data from the first detector layer to backplane electronics;
a first set of electronics disposed adjacent the first interconnect structure, wherein the first set of electronics is in operative association with the first interconnect structure and configured to process the first set of image data;
at least a second detector module, comprising:
a second detector layer having a top side and a bottom side, wherein the second detector layer comprises a plurality of second coupling gaps configured to facilitate passage of the first interconnect structure from the first detector layer to the backplane electronics;
a second interconnect structure operationally coupled to the second detector layer and configured to facilitate transfer of a second set of image data from the second detector layer to the backplane electronics; and
a second set of electronics disposed adjacent the second interconnect structure, wherein the second set of electronics is in operative association with the second interconnect structure and configured to process the second set of image data.

16. The detector assembly of claim 15, wherein the plurality of first coupling gaps in the first detector layer is configured to permit coupling between the top and bottom sides of the first detector layer.

17. The detector assembly of claim 15, further comprising a plurality of connectors configured to couple each of the first interconnect structure and the second interconnect structure to the backplane electronics.

18. The detector assembly of claim 15, wherein the first detector module is disposed adjacent the second detector module to form a detector sub-group.

19. The detector assembly of claim 15, further comprising a first backplane operatively coupled to the first detector module.

20. The detector assembly of claim 15, further comprising a second backplane operatively coupled to the second detector module.

21. The detector assembly of claim 15, wherein the plurality of second coupling gaps in the second detector layer is substantially larger than the plurality of first coupling gaps in the first detector layer.

22. The detector assembly of claim 15, further comprising a support structure configured to support each of the first detector module and the second detector module.

23. The detector assembly of claim 22, wherein the support structure comprises a plurality of slots configured to facilitate routing of each of the interconnect structures from the first detector module and the second detector module.

24. The detector assembly of claim 23, wherein each of the first detector module and the second detector module is aligned and fixed to the support structure.

25. The detector assembly of claim 22, further comprising a collimator aligned and fixed to a detector rail.

26. The detector assembly of claim 15, wherein a plurality of first detector modules and a plurality of second detector modules are tiled to assemble a large area detector assembly.

27. A method of imaging comprising:
obtaining a first set of image data from a first detector layer in a detector assembly having a first detector layer and at least a second detector layer, wherein the first detector layer comprises a plurality of first coupling gaps;
obtaining a second set of image data from a second detector layer, wherein the second detector layer comprises a plurality of second coupling gaps configured to facilitate passage of a first interconnect structure from the first detector layer to backplane electronics; and interpolating the second set of image data.

28. The method of claim 27, further comprising combining the first set of image data and the second of image data to form a combined image data set.

29. The method of claim 28, further comprising processing the combined image data to facilitate generating an image for display.

30. The method of claim 27, further comprising processing the first set of image data to generate a first image.

31. The method of claim 27, further comprising processing the second set of image data to generate a second image.

32. The method of claim 31, further comprising combining the first image and the second image to form a combined image for display.

33. The method of claim 32, further comprising applying a material discrimination algorithm to the combined image.

34. The method of claim 27, further comprising irradiating the first detector layer and the second detector layer with a source of radiation.

35. An imaging system comprising:
  a source of radiation configured to emit a stream of radiation toward a patient to be scanned;
  a computer configured to generate images with enhanced image quality and to provide tissue composition information;
  a detector assembly configured to detect the stream of radiation and to generate one or more signals responsive to the stream of radiation, wherein the detector assembly comprises:
    a first detector layer having a top side and a bottom side wherein the first detector layer comprises a plurality of first coupling gaps;
    a first interconnect structure operationally coupled to the first detector layer and configured to facilitate transfer of a first set of data from the first detector layer to backplane electronics;
    a second detector layer having a top side and a bottom side and disposed adjacent the bottom side of the first detector layer, wherein the second detector layer comprises a plurality of second coupling gaps configured to facilitate passage of the first interconnect structure from the first detector layer to the backplane electronics;
    a second interconnect structure operationally coupled to the second detector layer and configured to facilitate transfer of a second set of data from the second detector layer to the backplane electronics;
  a system controller configured to control the rotation of the source of radiation and the detector assembly and to control the acquisition of one or more sets of projection data from the detector assembly via a data acquisition system; and
  a computer system operationally coupled to the source of radiation and the detector assembly, wherein the computer system is configured to receive the one or more sets of projection data.

36. The system of claim 35, wherein, the computer system is further configured to combine the projection data with material decomposition and reconstruction algorithms.

* * * * *